United States Patent [19]

Kompolthy et al.

[11] 3,954,532
[45] May 4, 1976

[54] EXPLOSIVE COMPOSITIONS OF HIGH THERMAL STABILITY

[75] Inventors: Tivadar Kompolthy; Gyözö Bencz; János Deres, all of Budapest, Hungary

[73] Assignees: Vegyi- es Robbanoanyagipari Felugyelet; Orszagos Koolaj- es Gazipari Troszt, both of Budapest, Hungary

[22] Filed: Dec. 27, 1973

[21] Appl. No.: 428,752

[30] Foreign Application Priority Data
Jan. 15, 1973 Hungary ................ RO694

[52] U.S. Cl. .................... 149/45; 149/74; 149/78; 149/105; 149/106; 149/107
[51] Int. Cl.² .................... C06B 31/00
[58] Field of Search ........ 149/74, 105, 106, 107, 149/45, 78

[56] References Cited
UNITED STATES PATENTS
3,166,567  1/1965  Carboni .................... 149/105 X

*Primary Examiner*—Stephen J. Lechert, Jr.

[57] ABSTRACT

The explosives, explosive mixtures or assemblies according to the invention contain at least one new nitrated 2,5,8-triphenyl-tris-triazolobenzene derivative of the general formula (I)

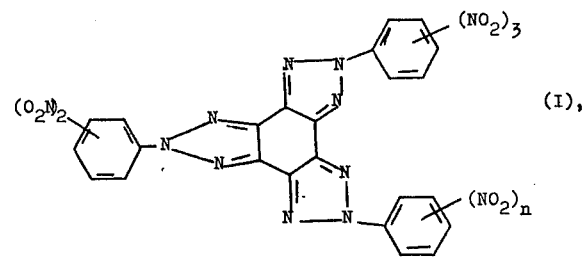

wherein $n$ represents an integer of two or three, or a nitromethane or nitric acid adduct of said compounds, and optionally contain known additives, too.

The thermal stabilities of these products are much better than that of the hitherto known brisant explosives, and at the same time their brisance and other explosive characteristics are satisfactory.

12 Claims, No Drawings

EXPLOSIVE COMPOSITIONS OF HIGH THERMAL STABILITY

This invention relates to explosive compositions or mixtures of high thermal stability, containing at least one new nitrated 2,5,8-triphenyl-tris-triazolobenzene derivative of the general formula (I)

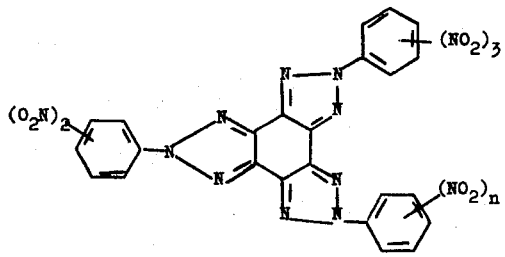

wherein $n$ represents an integer of two or three, or a nitromethane or nitric acid adduct of said compounds, and optionally one or more conventional additives.

This invention relates further to explosive devices and assemblies prepared with such compositions.

As it is known, steadily increasing requirements are set forth against the quality of explosive compositions regarding primarily their thermal stability, mainly in the deep drilling in mineral oil industry, but also at other technical fields.

German Pat. No. 1 164 900 describes thee tetranitro-dibenzo-1,3$a$, 4,6$a$-tetraazapentalene, which, according to the specification, has a similar grade of brisance than pentaerythrite tetranitrate, has a thermal stability even better than that of hexogene, and can be stored at 316°C for 4 hours.

This invention aims at novel explosive compositions or mixtures as well as at assemblies prepared with such compositions having similar explosive properties than the hitherto known brisant explosives, but exhibiting far better thermal stability.

In the course of our experiments we have found that the thermal stability of 2,5-bis-(2,4-dinitrophenyl)-8-(2,4,6-trinitrophenyl)-tris-triazolobenzene and of 2-(2,4-dinitrophenyl)-5,8-bis-(2,4,6-trinitrophenyl)-tris-triazolobenzene is much better than that of the hitherto known brisant explosives, and at the same time their brisance and other explosive properties are satisfactory. These compounds, moreover, can be prepared in an easy and economic way, and from these explosives assemblies with thermal stabilities superior to any of the known assemblies can be prepared.

Accordingly, this invention relates to explosive compositions or mixtures of high thermal stability, as well as to explosive devices and assemblies prepared with such compositions, characterized by containing at least one new nitrated 2,5,8-triphenyl-tris-triazolobenzene derivative of the general formula (I)

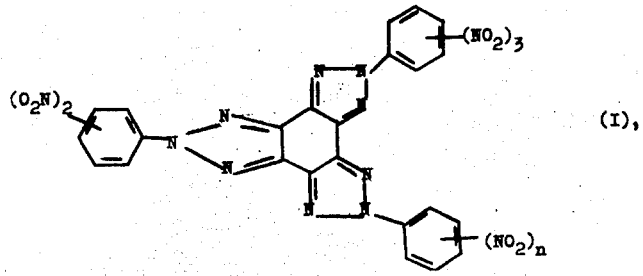

wherein $n$ represents an integer of two or three, or a nitromethane or nitric acid adduct of said compounds, and optionally also containing known additives.

The new compounds, 2,5-bis-(2,4-dinitrophenyl)-8-(2,4,6-trinitrophenyl)-tris-triazolobenzene and 2-(2,4-dinitrophenyl)-5,8-bis-(2,4,6-trinitrophenyl)-tris-triazolobenzene, respectively, can be prepared by the conventional nitrating methods from 2,5,8-tris-(2,4-dinitrophenyl)-tris-triazolobenzene, the latter being also a novel compound. Thus, for example, 2,5,8-tris-(2,4-dinitrophenyl)-tris-triazolobenzene is dissolved in oil of vitriol containing 40 percent of sulphuric trioxide, the solution is heated to 60°C, a nitrating acid consisting of 100 percent sulphuric acid and 98 percent nitric acid is added to the stirred mixture at the same temperature, thereafter the temperature of the mixture is raised gradually, within about 4 hours, to 90°, 110°, 130°, and 150°C, respectively, and finally the mixture is kept at this latter temperature for about 10 hours. Thereafter the reaction mixture is cooled, poured onto ice water, the separated nitro compound is filtered off, washed acid-free, dried, and recrystallized from a solvent, preferably from nitromethane or tetramethylsulphon, if desired. The hepta- or, respectively, octanitro-derivatives can be prepared separately by the proper selection of the sulphur trioxide and nitric acid content of the nitrating acid one may, however, also prepare a mixture containing the hepta- and octanitro compounds in arbitrary ratios.

2,5,8-tris-(2,4-dinitrophenyl)-tris-triazolobenzene, a new compound used as starting substance, can be prepared from the known 2,5,8-triphenyl-tris-triazolobenzene (Muzik, F., Allan, Z.J. : Chem. Listy 46, 774 /1952/) by conventional nitration procedures. According to another method 2,5,8-tris-(2,4-dinitrophenyl)-tris-triazolobenzene is prepared as follows: ortho- and-/or paranitroaniline is diazotated in the presence of a solvent, such as in dimethylformamide or dimethylacetamide, thereafter a solution, preferably an aqueous pyridine solution, of 1,3,5-triaminobenzene is added to the diazotated mixture, ensuring that the temperature does not exceed +5°C. In this reaction the 1,3,5-triamino-2,4,6-tri-(nitrophenylazo)-benzene corresponding to the starting diazotated nitroaniline compound is obtained, which is oxidized after isolation or in the reaction mixture itself with an appropriate oxidizing agent, preferably with copper sulphate. The oxidized product is the 2,5,8-tris-(nitrophenyl)-tris-triazolobenzene corresponding to the diazotated nitroaniline compound. The obtained 2,5,8-tris-(nitrophenyl)-tris-triazolobenzene can be subjected optionally to conventional nitration reactions to form 2,5,8-tris-(2,4-dinitrophenyl)-tris-triazolobenzene.

The new compounds, 2,5-bis-(2,4-dinitrophenyl)-8-(2,4,6-trinitrophenyl)-tris-triazolobenzene, and 2-(2,4-dinitrophenyl)-5,8-bis-(2,4,6-trinitrophenyl)-tris-triazolobenzene, respectively, can also be obtained via the direct nitration of the known compound, 2,5,8-tris-(2,4-dinitrophenyl)-tris-triazolobenzene. Nitration is carried out by conventional methods, it is preferred, however, to carry out the procedure stepwise, with nitrating acids of gradually increasing strengths.

We have found by the structure analysis of the product that several isomers of 2,5-bis-(2,4-dinitrophenyl)-8-(2,4,6-trinitrophenyl)-tris-triazolobenzene exist. The most important properties of the isomers, such as thermal stabilities and explosive characteristics, however do not differ from each other. Lower or higher amounts of each of the isomers are formed in the reaction. Accordingly, this invention also relates to explosives and assemblies containing the pure isomers of 2,5-bis-(2,4-dinitrophenyl)-8-(2,4,6-trinitrophenyl)-tris-triazolobenzene or any mixtures of these isomers; and the term "2,5-bis-(2,4-dinitrophenyl)-8-(2,4,6-trinitrophenyl)-tris-triazolobenzene" is to denote both the individual isomers and the mixtures thereof.

Some nitromethane or nitric acid adducts of 2-(2,4-dinitrophenyl)-5,8-bis-(2,4,6-trinitrophenyl)-tris-triazolobenzene have been described as UV-stablizers.

These adducts contain two moles of 2-(2,4-dinitrophenyl)-5,8-bis-(2,4,6-trinitrophenyl)-tris-triazolobenzene and 3 moles of nitromethane or nitric acid, and are formed when 2-(2,4-dinitrophenyl)-5,8-bis-(2,4,6-trinitrophenyl)-tris-triazolobenzene is brought into contact with nitromethane or nitric acid, respectively. The thermal stabilities and explosive characteristics of these adducts are similar to those of the octanitro compound, accordingly this invention also relates to explosives and assemblies containing the nitric acid or nitromethane adduct of 2-(2,4-dinitrophenyl)-5,8-bis-(2,4,6-trinitrophenyl)-tris-triazolobenzene.

The term "additive" used in the specification is to cover all the known substances used in the preparation of brisant explosives and assemblies able to influence favorably their properties at the appropriate field of use. It is required that the thermal stabilities of these additives are satisfactory at the working temperature of the brisant explosives.

Such additives are, for example, substances increasing the compressibility and oxygen balance of the brisant explosives, or increasing the adhesive forces of pressed articles, or decreasing the static charge. Graphite is, for example, an agent suitable to decrease the static charge formed in the brisant explosives. Molybdenium disulphide, added preferably in an amount of 0.1 5percent, improves the compressibility of the explosive, and several aromatic polynitro compounds, such as symm.trinitrobenzene, trinitrotoluene or hexanitrostilbene have similar properties. Even some percents of these additives decrease the pressure required to compress the mass without affecting the thermal stability of the explosive mixture essentially. If, however, it is not necessary to use the explosives at the upper limit of their thermal stabilities, these additives can even be used in as high amounts as 40 to 60 percent, and thus the product becomes far less expensive. If polynitro additives are used in such high amounts, it is preferred to add simultaneously a gellifying substance to the mixture in order to prevent the melting or liquefaction of the explosive mixture at the working temperature. As gellifying agents, preferably colloidal silicic acids can be used, which can also be subjected to a preliminary surface treatment, if necessary.

For several fields of use the explosives according to the invention are to be converted into uncoated assemblies (pressed articles) of pre-determined shape and dimensions. In this event a binding agent is preferably used as additive. These binding agents may be mineral substances, such as sodium or potassium silicates, but organic compounds, preferably polymers of high thermal stabilities, such as silicons, polyester resins, polyimides, etc., can equally be used.

Similarly to the known explosives, also the explosives according to the invention contain low amounts of oxygen. In order to improve the oxygen balance it is preferred to add mineral compounds of high oxygen contents, such as potassium perchlorate or lead nitrate, to the mixture. These compounds essentially do not affect the explosive characteristics of the explosives according to the invention.

The new explosives and assemblies prepared therefrom are described in more detail in the following non-limiting Examples.

In the tables of the Examples the following designations were used:
  substance No. 1: 2,5-bis-(2,4-dinitrophenyl)-8-(2,4,6-trinitrophenyl)-tris-triazolobenzene;
  substance No. 2: a mixture containing 20 percent of 2,5-bis-(2,4-dinitrophenyl)-8-(2,4,6-trinitrophenyl)-tris-triazolobenzene and 80 percent of 2-(2,4-dinitrophenyl)-5,8-bis-(2,4,6-trinitrophenyl)-tris-triazolobenzene;
  substance No. 3: 2-(2,4-dinitrophenyl)-5,8-bis-(2,4,6-trinitrophenyl)-tris-triaolobenzene;
  reference substance: tetranitro-dibenzo-1,3a,4, 6a-tetraazapentalene.

The percentage values indicated in the Examples represent percents by weight.

EXAMPLE 1

0.25 g. samples of 2,5-bis-(2,4-dinitrophenyl)-8-(2,4,6-trinitrophenyl)-tris-triazolobenzene, of a mixture containing 20 percent of 2,5-bis-(2,4-dinitrophenyl)-8-(2,4,6-trinitrophenyl)-tris-triazolobenzene and 80 percent of 2-(2,4-dinitrophenyl)-5,8-bis-(2,4,6-trinitrophenyl)-tris-triazolobenzene, of 2-(2,4-dinitrophenyl-5,8-bis-(2,4,6-trinitrophenyl)-tris-triazolobenzene, and of tetranitro-dibenzo-1,3a,4,6a-tetraazapentalene, respectively, were filled into aluminum tubes of 64 mm. diameter and 43 mm. length (10 tubes each). The explosives were weighted with an accuracy of 0.1 mg. The filled tubes were compressed under a force of 225 kg., thereafter 0.20 g. amounts (weighed with an accuracy of 0.1 mg.) of the same explosives were introduced into each of the tubes, and the contents of the tubes were compressed with a force of 100 kg.

The tubes containing the explosives were then measured by an analytical balance, heated to 300 ±3°C or 325 ±3°C, respectively, in 3 hours, under the necessary safety measures, and were kept at the same temperature for 2, 4, 6, and 10 hours, respectively. Thereafter the heat-stored tubes were cooled and weighed again on analytical balance.

The percentage weight losses occuring at heat-storage are given in Table 1.

Table 1

| Temperature °C | Time hours | Weight loss in percents | | | |
|---|---|---|---|---|---|
| | | Substance No.1 | Substance No.2 | Substance No.3 | Reference substance |
| 300 | 2 | 0.91 | 1.83 | 1.47 | 1.17 |
| | 4 | | 1.87 | 1.55 | 1.52 |
| | 6 | | 2.14 | 1.73 | 1.88 |
| | 10 | | 3.05 | 2.67 | 2.50 |
| 325 | 2 | | 4.13 | 3.66 | 4.82 |
| | 3 | | | | deflagrates |
| | 4 | | 11.67 | 8.82 | |
| | 5 | | deflagrates | | |
| | 5.5 | | | deflagrates | |

The data of Table 1 show that no significant differences can be observed between the reference substance and the substances tested [i.e., 2,5-bis-(2,4-dinitrophenyl)-8-(2,4,6-trinitrophenyl)-tris-triazolobenzene, a mixture containing 20 percent of 2,5-bis-(2,4-dinitrophenyl)-8-(2,4,6-trinitrophenyl)-tris-triazolobenzene and 80 percent of 2-(2,4-dinitrophenyl)5,8-bis-(2,4,6-trinitrophenyl)-tris-triazolobenzene, and 2-(2,4-dinitrophenyl)-5,8-bis-(2,4,6-trinitrophenyl)-tris-triazolobenzene, respectively] at 300°C. At 325°C, however, the thermal stabilities of the explosives or explosive mixtures according to the invention are significantly superior to that of tetranitro-dibenzo-1,3a,4-,6a-tetraazapentalene, the compound with the best thermal stability of the known explosives. Namely, this latter compound deflagrates even after 3 hours of storage, while 2-(2,4-dinitrophenyl)-5,8-bis-(2,4,6-trinitrophenyl)-tris-triazolobenzene, an explosive according to the invention, can be heat-stored for 5 hours even at 325°C, and deflagration occurs only after 5.5 hours of storage.

EXAMPLE 2

0.5 g. of lead azide are introduced into each of the aluminum tubes containing the brisant explosives heat-treated as described above, and the contents of the tubes are compressed with a force of 125 kg. The thus-obtained blasting caps are initiated in the conventional manner, each cap being initiated in the same way. The explosive capacities of the caps were examined by lead puncture test, and the explosive capacities of the heat-stored caps were compared to those of 10 caps prepared similarly but not subjected to heat storage. The comparison was based on the following calculation: the explosive capacities (lead puncture) of the not heat-stored caps were regarded as 100, and those of the heat-stored caps (i.e., the diameters of the holes formed after the explosion) were related to this value.

The thus-obtained percentage values, averaged for 10 caps, are listed in Table 2.

Table 2

| Temperature °C | Time hours | Lead puncture | | | |
|---|---|---|---|---|---|
| | | Substance No.1 | Substance No.2 | Substance No.3 | Reference substance |
| 300 | 2 | 99 | 99 | 97 | 97.5 |
| | 4 | | 92 | | 95 |
| | 6 | | 82 | | 85 |
| | 10 | | 73.5 | 89 | 84 |
| 325 | 2 | | | 86 | 70 |
| | 3 | | | | deflagrates |
| | 4 | | | 65 | |

The data of Table 2 show that no significant difference can be observed between the lead punctures of the caps made of the explosives according to the invention and of the reference substance (tetranitro-dibenzo-1,3a,4, 6a-tetraazopentalene), respectively, after a heat storage at 300°C. On the other hand, after a 2 hours' heat storage at 325°C the lead puncture of the reference substance is significantly smaller than that of substance No. 3. Further comparisons cannot be carried out, since the reference substance detonates after 3 hours' heat storage at 325°C, while substance No. 3 exhibits a significant explosive capaci y even after a 4 hours' heat storage at 325°C.

EXAMPLE 3

Aluminum tubes (10 tubes each) are filled with brisant explosives as described in Example 1. Prior to the heat storage 0.5 g. of lead azide with a particular thermal stability, prepared as described in Hungarian Pat. No. 151,422, were introduced into each of the tubes, and the contents of the tubes were compressed with a force of 125 kg. The thus-obtained caps were heat-stored at 260°, 280° and 300°C, respectively, using a heating rate of 1.6°C/min.

After a 2 hours' heat storage at 260°C the caps were cooled and each cap was initiated in the same conventional way. Their explosive capacities were examined as described in Example 2. In this test each of the caps exhibited similar, excellent characteristics.

The caps containing substances Nos. 2 and 3, respectively, were re-examined after a 2 hours' heat storage at 280°C. The lead puncture values of the heat-stored caps were 90 percent of those containing the same explosive but not subjected to heat storage. On the other hand, the caps containing the reference substance deflagrate after a storage of 1 hour 55 minutes at this temperature.

Caps containing substance No. 3 were heated to 300°C in 3 hours, maintaining an even heating rate, and the caps were stored at this temperature. The caps were stable at 300°C for 37 minutes, and deflagrated only after this time.

EXAMPLE 4

2-(2,4-dinitrophenyl)-5,8-bis-(2,4,6-trinitrophenyl)-tris-triazolobenzene (substance No. 3), and tetranitrodibenzo-1,3a,4,6a-tetraazapentalene (reference substance), respectively, were filled separately into aluminum tubes, and detonating cords were prepared from the respective explosives by the conventional technique. The outer diameter of a ready detonating cord is 4.90 mm., and the inner diameter 4.15 mm., the core densities of the detonating cords, however, are different, since the specific core weight of the cord made of the explosive according to the invention is 1.33 g./cm³, while that of the cord made of the reference substance is 1.43 g./cm³. The detonation velocities of the individual detonating cords were measured by the Dautrich method, and the results were calculated on the basis of the five measurements. The following means values were obtained:

| | |
|---|---|
| substance No.3 | 6050 m./sec. |
| reference substance | 5840 m./sec. |

Accordingly, the detonation velocity of substance No. 3 is better than that of the reference substance, despite the fact that the specific core weight of the cord containing the former substance is significantly lower.

EXAMPLE 5

25 g. samples of a mixture containing 20 percent of 2,5-bis-(2,4-dinitrophenyl)-8-(2,4,6-trinitrophenyl)-tris-triazolobenzene and 80 percent of 2-(2,4-dinitrophenyl)-5,8-bis-(2,4,6-trinitrophenyl)-tris-triazolobenzene (substance No. 4,62) and of tetranitro-dibenzo-1,3a,4,6a-tetraazapentalene (reference substance), respectively, were filled into conventional metal tubes (five tubes each) usable for perforation, and the assemblies were compressed in an appropriate hydraulic press under a pressure of 2300 kg./cm³. The perforators were shot into steel targets placed in a distance of 30 mm. The results are listed in Table 3.

Table 3

| | Substance No.2 | Reference substance |
|---|---|---|
| Depth of penetration, mm. | 51.9 | 51.5 |
| Hole diameter at the site of penetration, mm. | 11.5 | 10.6 |

The data of the Table show that the results obtained with substance No. 2 are more favorable.

EXAMPLE 6

Five caps were prepared from 85 percent of 2-(2,4-dinitrophenyl)-5,8-bis-(2,4,6-trinitrophenyl)-tris-triazolobenzene (substance No. 3) and 15 percent of potassium chlorate in a way described in Example 2, and their explosive capacities were examined. Five other caps, used as controls, were filled with substance No. 3 alone, otherwise treated as the above ones. The caps were deflagrated as described in Example 2, without subjecting them to a preliminary heat storage. The mean lead puncture value of the caps containing potassium perchlorate, related to that of the control caps, is 97 percent.

What we claim is:

1. An explosive composition or mixture of high thermal stability, comprising at least one nitrated 2,5,8-triphenyl-tris-triazolobenzene derivative of the general formula (I)

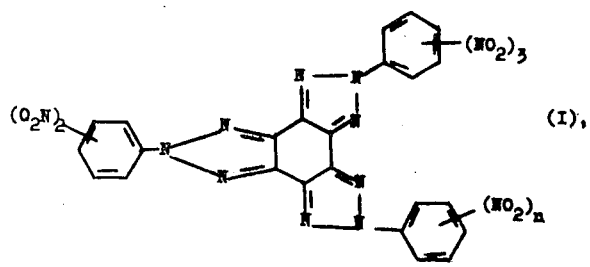

wherein $n$ represents an integer of two or three, or a nitromethane or nitric acid adduct thereof.

2. A product as claimed in claim 1, in which the nitrated compound is 2,5-bis-(2,4-dinitrophenyl)-8-(2,4,6-trinitrophenyl)-tris-triazolobenzene.

3. A product as claimed in claim 2, in which the nitrated compound is a pure isomeric 2,5-bis-(2,4-dinitrophenyl)-8-(2,4,6-trinitrophenyl)-tris-triazolobenzene, or an isomeric mixture of arbitrary composition.

4. A product as claimed in claim 1, in which the nitrated compound is 2-(2,4-dinitrophenyl)-5,8-bis-(2,4,6-trinitrophenyl)-tris-triazolobenzene.

5. A product as claimed in claim 1, in which the nitrated compound is a nitric acid adduct of 2-(2,4-dinitrophenyl-5,8-bis-(2,4,6-trinitrophenyl)-tris-triazolobenzene.

6. A product as claimed in claim 1, in which the nitrated compound is a nitromethane adduct of 2-(2,4-dinitrophenyl)-5,8-bis-(2,4,6-trinitrophenyl)-tris-triazolobenzene.

7. A product as claimed in claim 1, which further comprises an additive selected from the group consisting of antistatics, pressing aids, gellifying agents, binding agents, and substances improving the oxygen balance.

8. A product as claimed in claim 1, in which the antistatic agent is graphite.

9. A product as claimed in claim 8, in which the pressing aid is at least one substance selected from the group consisting of polynitro compounds, such as symm. trinitrobenzene, trinitrotoluene, or hexanitrostilbene, and molybdenum disulphide.

10. A product as claimed in claim 8, in which the gellifying agent is colloidal silicic acid.

11. A product as claimed in claim 8, in which the binding agent is at least one substance selected from the group consisting of sodium silicates, calcium silicates, silicones, polyester resins and polyimides.

12. A product as claimed in claim 8, in which the substance improving the oxygen balance is at least one selected from the group consisting of potassium perchlorate and lead nitrate.

* * * * *